(12) United States Patent
Smith et al.

(10) Patent No.: US 6,561,966 B1
(45) Date of Patent: May 13, 2003

(54) DEVICE FOR X-RAY DOSAGE CONTROL

(75) Inventors: Leif Smith, Uppsala (SE); Lars Tenerz, Uppsala (SE); Jonas Tiren, Uppsala (SE)

(73) Assignee: Radi Medical Technologies AB, Uppsala (SE)

( * ) Notice: Subject to any disclaimer, the term of this patent is extended or adjusted under 35 U.S.C. 154(b) by 139 days.

(21) Appl. No.: 09/680,512

(22) Filed: Oct. 6, 2000

Related U.S. Application Data (63) Continuation-in-part of application No. 09/585,283, filed on Jun. 2, 2000, now Pat. No. 6,477,233
(60) Provisional application No. 60/137,478, filed on Jun. 4, 1998.

(51) Int. Cl.⁷ .............................. A61N 5/00; A61M 36/12
(52) U.S. Cl. ........................................................ 600/3
(58) Field of Search ........................... 600/1–8; 128/427

(56) References Cited

U.S. PATENT DOCUMENTS

| | | | |
|---|---|---|---|
| 3,866,050 A | 2/1975 | Whitfield | |
| 4,851,694 A | 7/1989 | Rague et al. | |
| 5,084,001 A * | 1/1992 | Van't Hooft et al. | 250/497.1 |
| 5,092,834 A * | 3/1992 | Bradshaw et al. | 600/3 |
| 5,139,473 A * | 8/1992 | Bradshaw et al. | 600/3 |
| 5,213,561 A * | 5/1993 | Weinstein et al. | 600/3 |
| 5,302,168 A * | 4/1994 | Hess | 600/3 |
| 5,350,101 A | 9/1994 | Godlewski | |
| 5,540,659 A * | 7/1996 | Teirstein | 600/3 |
| 5,733,277 A | 3/1998 | Pallarito | |
| 5,800,333 A * | 9/1998 | Liprie | 600/3 |
| 5,851,172 A | 12/1998 | Bueche et al. | |
| 5,854,822 A * | 12/1998 | Chornenky et al. | 378/122 |
| 5,899,882 A | 5/1999 | Waksman et al. | |
| 6,033,357 A * | 3/2000 | Ciezki et al. | 600/3 |

FOREIGN PATENT DOCUMENTS

| | | |
|---|---|---|
| EP | 0 791 374 | 8/1997 |
| EP | 0 867 200 | 9/1998 |
| WO | 98/36796 | 8/1998 |
| WO | 99/11325 | 3/1999 |

\* cited by examiner

*Primary Examiner*—Samuel G. Gilbert
(74) *Attorney, Agent, or Firm*—Foley & Lardner (57) ABSTRACT

The invention relates to an apparatus for the controlled delivery of ionizing radiation to a therapy location. It comprises a source (4) of ionizing radiation provided at the distal end of an elongated member (6). It also has a control unit (12) for controlling the movement of said radiation source (4) at the therapy location, via a driving unit (21, 22; 23, 24, 25, 26). A method according to the invention comprises controlling the radiation dose at the therapy location, by controlling the movement of the source.

14 Claims, 9 Drawing Sheets

DEVICE FOR X-RAY DOSAGE CONTROL

The Applicants hereby claim the benefit of U.S. Application Ser. No. 09/585,283, filed Jun. 2, 2000, and U.S. provisional application Ser. No. 60/137,478 filed Jun. 4, 1999. The content of these two applications and EP Application 99850222.3 filed Jun. 7, 1999, are incorporated herein by reference.

The present invention relates generally to systems and devices for delivering controlled doses of X-rays to therapy locations in a human or animal body.

BACKGROUND OF THE INVENTION

For several medical therapy situations it is necessary to expose a lesion of some sort to radiation in order to be able to remedy the problem.

As an example, traditionally a stenosed coronary artery is often treated by balloon dilatation, i.e. Percutaneous Transluminal Coronary Angioplasty (PTCA). A small balloon at the top of a plastic catheter is inserted into the femoral artery, guided in the vessels to the site of the stenosis, and inflated. As the stenosis is pushed out by the balloon, the artery is widened to normal inner diameter. In order to further improve the treatment, a so called stent is mostly positioned at the location of the stenosis. However, in about one third of the patients, a restenosis will still occur after the PTCA was performed.

One means of reducing the restenosis rate is to treat the vessel wall locally with X-ray, gamma or beta radiation in conjunction with the PTCA. The exact mechanism by which radiation inhibits restenosis is not yet fully understood. However, a radiation dose amounting to about 10–50 Gy from catheterised gamma and beta (radiation) sources have been shown to lower the restenosis rate substantially in several trials.

Conventionally, radioactive sources, e.g. in the form of radioactive nuclides have been used to supply the required radiation. In cases where a lesion has varying extensions and thicknesses in different directions inside a vessel, it can be very difficult to provide a radiation dose tailored to the lesion at hand. The prior art methods and devices are based on the provision of a plurality of radioactive isotopes (nuclides), arranged in a row, as disclosed in e.g. U.S. Pat. No. 5,899,882 (Novoste Corp.). The major disadvantage with this method is that the length cannot, or at least only with difficulty can, be adapted to the actual case. If, for example, an irradiation device provided with isotopes over a length of 4 mm, is used to irradiate a lesion of 3 mm length, it goes without saying that healthy tissue will be undesirably exposed to radiation.

In order to achieve a rotationally symmetric and uniform irradiation, various mechanical methods and means have been used in the prior art. These prior art means are provided for the centering of the radiation source in a vessel mechanically, e.g. by suitable spacer means.

In contrast to radioactive sources, e.g. in the form of said radioactive nuclides, in applicants' U.S. patent application Ser. No. 08/805,296 (corresponding to WO 98/36796), incorporated herein, in its entirety, by reference, there is disclosed a miniaturized source of ionizing electromagnetic radiation, comprising a pair of plates; a hermetically sealed microcavity formed in one of the plates; a pair of electrodes in the form of a cathode and an anode, at least one electrode being located in the microcavity and the other electrode being located on the other plate; the anode being at least partly of a metal having a relatively high atomic weight; and electrically conducting leads connected to the cathode and the anode. Furthermore, in applicants' U.S. provisional application 60/137,478 (corresponding to Swedish patent application no. 9902118-0) there is also suggested an X-ray source that is possible to switch on and off electronically.

Another device is based on a balloon catheter for dilatation, but where the balloon is filled with radioactive liquid through the catheter lumen. This device has a disadvantage in that there is a risk that radioactive liquid inadvertently could come out into the surroundings.

Still another approach is to cover the balloon of a balloon catheter device with a radioactive coating.

As touched upon already, a problem that the prior art devices suffer from is the difficulty of controlling the dosage delivered, in spatial terms. I.e. in view of the fact that the individual radiation sources in U.S. Pat. No. 5,899,882 (Novoste) essentially are point sources, in order to cover a larger area, there must be provided a plurality of point sources on a guide wire. This could be difficult from a manufacturing point of view, and also the assembly of several X-ray source will be relatively bulky if a large number of radiation sources are provided, and this could cause difficulties in the manipulation of the guide wire e.g. inside the narrow coronary vessels.

Also, it may be crucial to deliver an exact amount of radiation, in that too much radiation kills cells, and too little radiation may cause cancers and other cell growth without actually achieving the desired treatment effect.

SUMMARY OF THE INVENTION

Thus an object of the present invention is to provide a device for delivering ionizing radiation (e.g. X-rays) to a therapy location, wherein the control of the dosage over the selected therapy region can be significantly improved. In particular the treated lesion should be subjected to a known and controlled radiation dose. Healthy tissue should not be subjected to significant radiation doses. By "controlled" is meant that the tissue will be subjected to a known amount of radiation at a given depth, regardless of the thickness of the lesion.

In order to solve the problem, the invention provides means for enabling the manipulation of a radiation source so as to change its position at the therapy location in order to control the dose in terms of the amount of radiation delivered and in terms of where it is delivered. Especially it enables the adjustment of its position in the longitudinal direction in a vessel, when radiation is to be provided over a larger area than is covered by the radiation lobe from an individual radiation source. Furthermore, the invention provides for the rotation of the source inside a vessel.

The object indicated above is achieved with a device as claimed in claim 1.

In a further aspect the invention concerns a method of providing a controlled dose of ionizing radiation to a lesion at a therapy location, the method being defined in claim 10.

Embodiments specifically addressing various problems are defined in the dependent claims.

DETAILED DESCRIPTION OF THE PREFERRED EMBODIMENTS

Figure 1A:
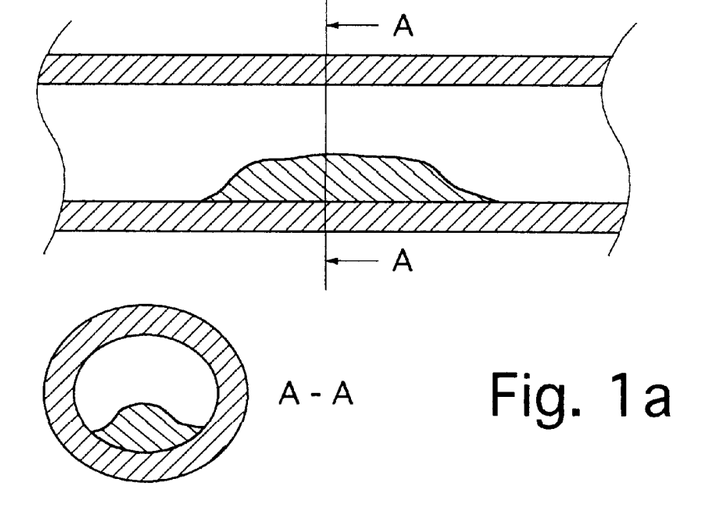
FIG. 1a is a cross section through a vessel with a stenosis.
Figure 1B:
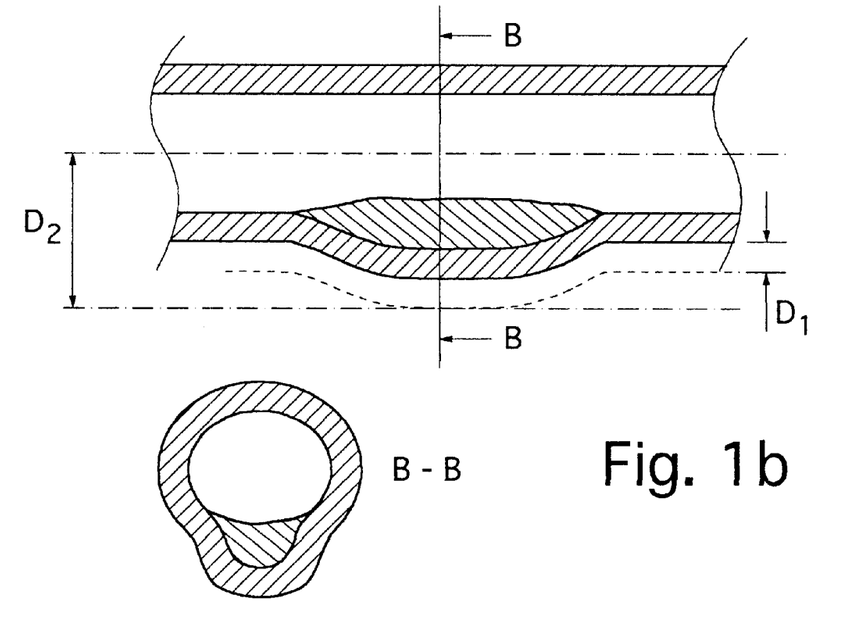
FIG. 1b is a cross section of a vessel after performed PTCA.

First the PTCA procedure will be discussed in some more detail. As already mentioned a balloon catheter is used to dilate a vessel at the stenosis. In this process the stenosis will be forced away from the vessel interior, as shown in FIGS. 1a (illustrating a stenosis before PTCA treatment), and 1b (after PTCA treatment). However, this treatment has the effect that the vessel tissue will be stretched and sometimes will even rupture. This will frequently cause scar growth, and thus after the PTCA often times restenosis will occur, i.e. the tissue will grow back inwards again, even if a stent has been inserted. The mechanism of the restenosis is not fully understood as already indicated. However, the effect of the above mentioned irradiation on the site of the stenosis is believed to be that the tissue adjacent the stenosis, i.e. vessel wall VW and other tissue outside the vessel, will be damaged. Thereby the growth rate is reduced. Thus, in order to damage the tissue, the radiation must first penetrate the stenosis (calcified plaque), and then still be sufficiently intense to cause the desired effect. One approach is to make sure that the radiation penetrates a certain distance beyond the lesion, into the tissue behind it, i.e. at a constant depth $D_1$ from the interface between the plaque and the vessel or other tissue, indicated by dashed line A. Another approach could be to require that the radiation penetrates to a constant depth $D_2$ from the center C of the vessel, and indicated by dash-dotted line B. Depending on the selected approach, the control unit has to be programmed correspondingly, but once the principle is understood, any approach an be taken without departing from the inventive idea.

Figure 2:
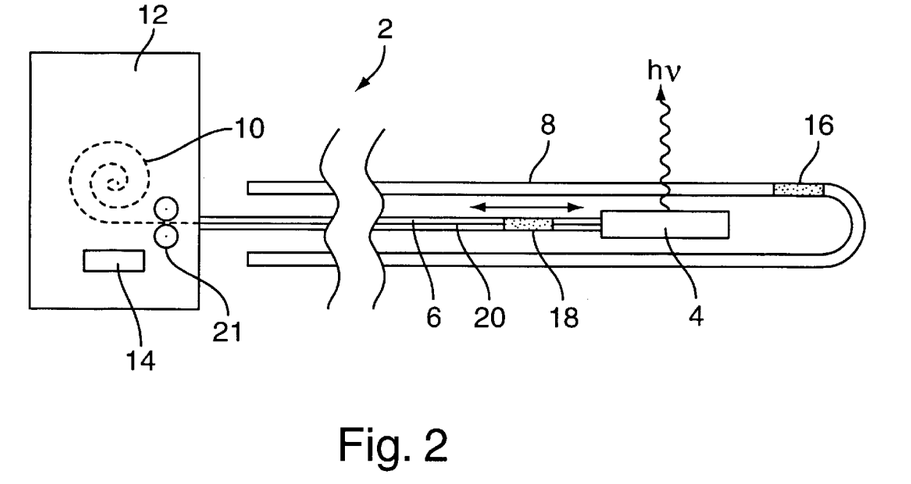
FIG. 2 shows schematically am apparatus according to the invention.

Now a device according to the invention will be described, and a schematic illustration is shown in FIG. 2, and generally designated with reference numeral 2. A radiation source, e.g. in the form of a miniature X-ray generating device (in the shown embodiment a device based on chip technology) 4 can be attached to a simple wire 6, running inside a catheter 8 (it should be noted, however, that for the purpose of the general concept of the invention, the source can be of any type, such as the conventionally used radioactive isotope, or an electrically energized X-ray source). The wire 6 can then easily be moved forward and backwards inside the lumen of the catheter, illustrated by arrows. This could be done manually, but in accordance with the invention there is provided a driving unit, e.g. a motor powered gear device (not shown) to enable programmed movement to and fro inside the catheter 8. This will be of great utility if it is desirable to provide radiation over a relatively extended lesion, where it is difficult if not impossible to provide a radiation source that covers the entire lesion. In a further embodiment there could also be provided means for rotating the radiation source. In combination with a longitudinal movement a spiral movement will be achieved.

In a still further embodiment the catheter is designed so as to seal off the interior and thereby to protect the patient from being exposed to the wire. By virtue of the catheter being sealed there is no need for sterilization of the wire and the radiation source, which thus can be made as a re-usable item, and also the handling will of course be much simpler when sterilization is not necessary.

The entire wire with the radiation source attached to the distal end could be provided on a spool or cylinder 10 arranged inside a control unit 12. This would provide adequate protection of the relatively sensitive device. An X-ray detector 14 can be provided inside the control unit, in the vicinity of said spool, whereby calibration or function checks can be performed within the control unit. This would require adequate radiation shields surrounding the location of the source.

Suitably the radiation source and/or the catheter are provided with some pieces 16, 18 of radiopaque material at the distal end portion, in order to be able to position the source accurately when it is inserted into a vessel.

If the wire 6 on which the radiation source is mounted is made of metal, it could be used as an electrical conductor for providing the activation voltage to the chip. The second conductor can be provided as a single lead 20 running parallel with the wire and suitably attached thereto. A coaxial type of structure is also conceivable where an insulator is provided around the core wire, and the second electrical conductor is provided as a concentric layer of conductive material on the insulator.

Figure 3:
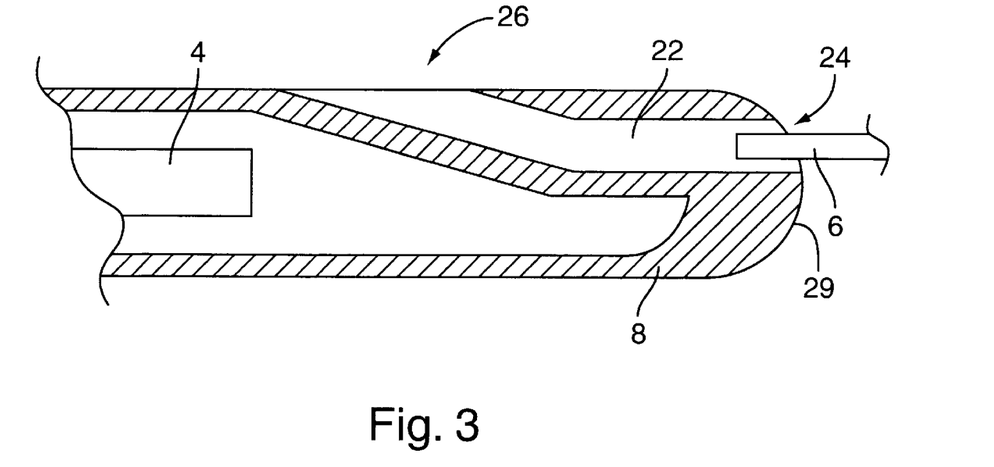
FIG. 3 shows the details of a catheter tip to be used with the invention.

A standard procedure for locating a catheter, i.e. to manipulate it to a selected therapy location inside the body of a patient, is to first insert a guide wire, which is flexible enough to be easily manipulated, to the location where the therapy is to be performed. The catheter to be used will have a small lumen 22 that is sealed from the rest of the catheter 8 interior where the radiation source 4 is to be located, as shown in FIG. 3. There will also be provided a first aperture 24 in distal tip 28 of the catheter for the access to said lumen, and a second aperture 26 in the side wall of the catheter. Thus, the catheter 8 can be threaded onto the (guide) wire 6, by inserting the proximal end of the (guide) wire through the aperture 24, and passing it through the lumen 22 to exit through the aperture 26. The catheter can then be fed along the guide wire to the desired location.

In the system disclosed in FIG. 2 the radiation source is illustrated as a small chip 4 from which the radiation will be emitted asymmetrically, i.e. with a higher intensity in one direction than in other directions, indicated by an arrow hv.

Figure 4:
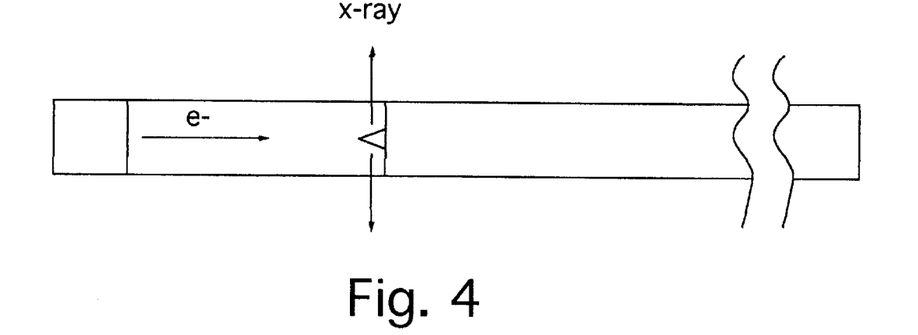
FIG. 4 is an example of a radiation source usable in the invention.

Another design principle for a radiation source is schematically illustrated in FIG. 4. Here the acceleration voltage is applied in the longitudinal direction of the source, and will therefore yield a radiation emission in radial direction to an equal extent (at least theoretically) around the entire circumference.

As indicated previously the operation of the device depends on the information about the lesion to be treated that is obtainable. Normally one or more of the following methods are used:

1) X-ray examinations; this will produce information about the topology of the lesion in the longitudinal direction, i.e. the length of the stenosis and its thicker and thinner parts. Also of course the exact location of the stenosis can be determined.
2) (intravascular) ultra-sonic investigations; by this method information can be obtained about the cross sectional area of the stenosis in the transverse direction of a vessel. By producing "images" of the stenosis cross section and adding them, a good picture of the spatial distribution of the stenosis can be obtained. Composition data is also obtainable by this method.
3) Information about the composition, i.e. the concentration of calcium (calcified plaque) can also be obtained by NMR techniques. The higher the concentration of Ca, the longer the required irradiation time will be, due to higher absorption.

Thus, it is possible to obtain quantified information about the location of a stenosis, its topology and its composition. This information can be fed into the control unit of the apparatus according to the invention, which, based on said information, will calculate a suitable treatment program, in terms of sweeping rate in the longitudinal direction of the radiation source inside the vessel, radiation intensity variations during the sweep in order to adapt to the specific topology at hand, and the concentration of calcified plaque in the lesion.

Now the various functions of the device will be described separately in closer detail.

As already indicated, in one embodiment, the longitudinal translational movement is achieved by employing a spool or cylinder onto which a (guide) wire having a radiation source attached to the distal end can be unwound and winded up. However, in a preferred embodiment it will be desirable to provide a couple of drive rolls 21 between which the (guide) wire 6 is to be passed, whereby a "pinch" is created, see FIG. 2. The rotation of the rolls is synchronized with the rotation of the spool 10. In this way, and by coupling the driving unit that drives the spool 10 (e.g. an electric motor 22), to the control unit, it is possible to accurately control the movement of the guide wire, in terms of speed and range of movement. The speed of movement can thus be controlled in correlation with the radiation intensity, such that a desired dose will be delivered to the lesion. The details of the control will be discussed further below.

It is also desirable to be able to rotate the radiation source at the therapy location. In particular this is necessary if the radiation source does not emit a uniform radiation in all directions. An ideal source would of course emit a perfect radiation profile, be it a point source emitting a lobe in essentially one direction, or a tube shaped source emitting radially in all directions.

Thus, in order to equalize the radiation emitted from the source it may be desirable to rotate it, thereby subjecting the lesion to a time averaged dose.

Figure 5A:
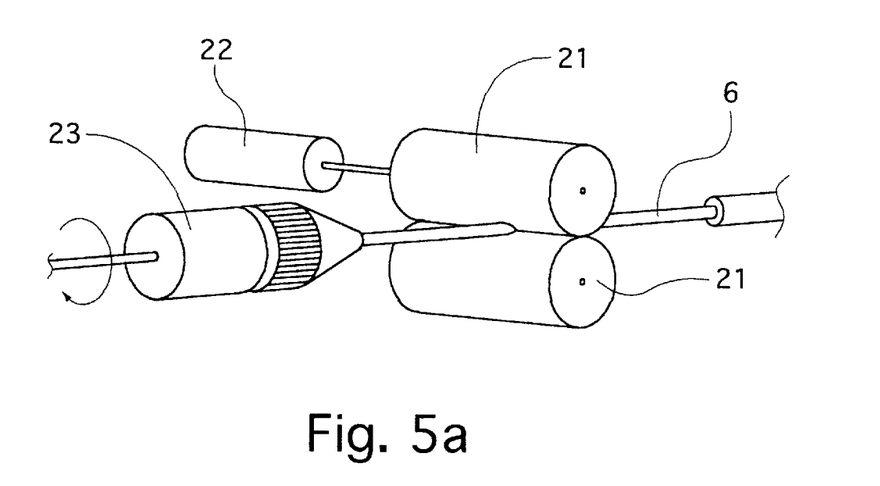
FIG. 5a is an embodiment of a mechanism for controlling the movement of a radiation source.
Figure 5B:
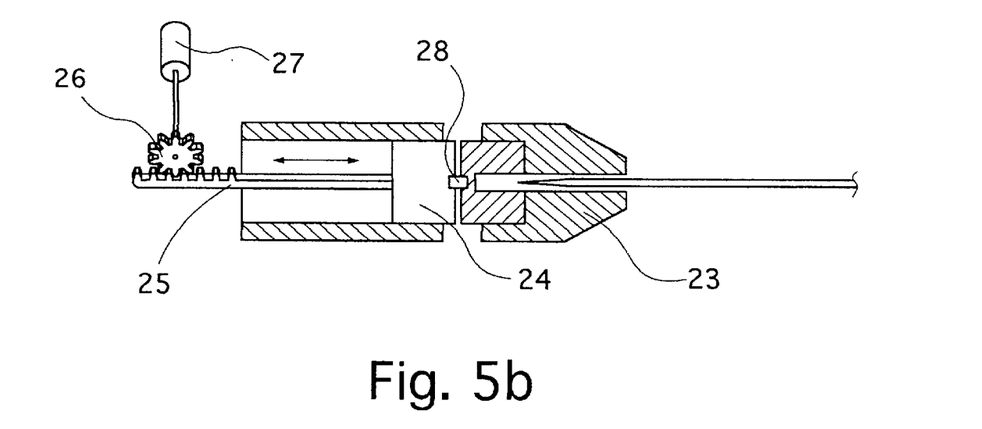
FIG. 5b is another embodiment of a mechanism for controlling the movement of a radiation source.

Rotation is most easily achieved if the entire wire on which the source is attached is unwound from the spool or cylinder mentioned above so as to leave the proximal end of the wire free. The free end is then mounted in a clamping device 23, e.g as shown in FIG. 5a. The clamping device itself is connected to a device for generating a rotational movement, such as an electric motor 24, via a coupling shaft or axle 28, as schematically illustrated in the figure. If it is desirable to subject the source to both a translation (longitudinal) movement and to a rotation, the clamping device can be attached in a telescoping manner to a rack gear 25, which is operated by a gear 26 connected to a motor 27, as indicated in FIG. 5b. In one alternative the guide rolls mentioned above, and used for the longitudinal movement, can be used in conjunction with the rotation device, in which case the telescoping device is passive. Instead of using the guide rolls for the longitudinal movement, the telescoping member can be actuated by a suitable motor to move backwards and forwards, to control the movement at the lesion.

Obviously, the rotation and translation can be achieved in many different ways, and the skilled man will most certainly be able to find a number of different solutions.

Figure 6:
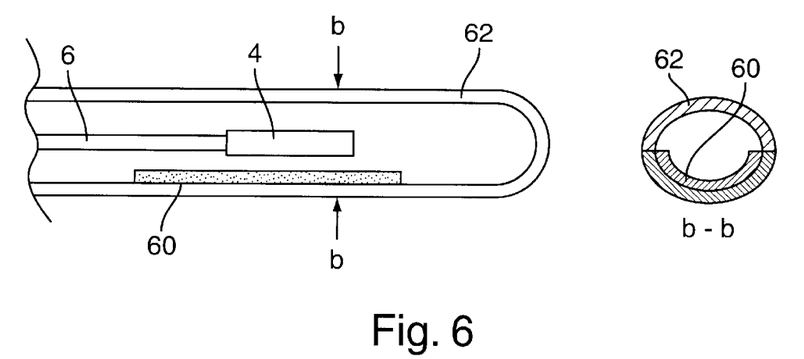
FIG. 6 shows a cross section of a catheter having a radiation shielding element.

As already mentioned, the rotation may be desirable in order to average out the dose over the lesion. However, e.g. a stenosis can often times be located only to one side of a vessel, in which case healthy tissue would be exposed unduly to radiation during rotation of the source 4. In order to avoid this to happen, it may be convenient to provide a radiation shield over a portion of the circumference of the catheter 62, as illustrated in FIG. 6. Equally well the source itself could be shielded, although the latter approach would cause manufacturing problems that the first approach would not exhibit. The shield is suitably provided as a layer or insert of some radiation opaque material, such as platinum or (Pt) or tungsten (W).

Figure 7:
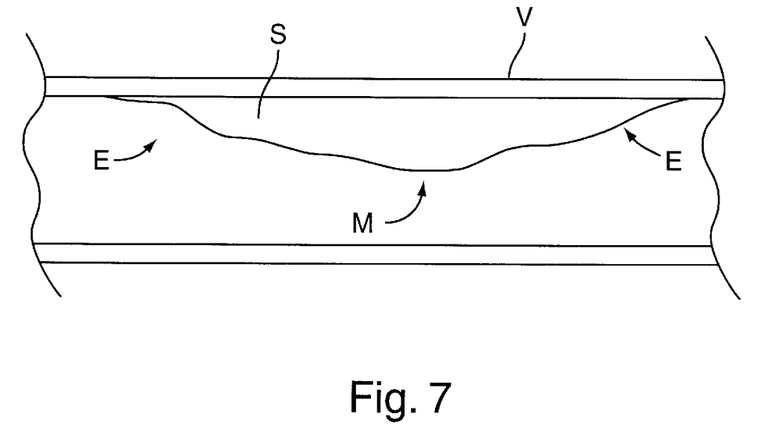
FIG. 7 shows an example of the topology of a stenosis.

Numerous possibilities exist for achieving the necessary correlation. Let us first consider a lesion that is localized to one side of a vessel V and has a topology such as that indicated in FIG. 7. In order that the same dose be delivered to both the thinner end portions E of the stenosis S, as well as to the thicker mid-portion M, either the speed of movement in the longitudinal direction can be varied such that the speed is highest at the ends, and continuously decreasing when the radiation source approaches the mid-portion. This would be the only possible solution if a radioactive isotope were used as the radiation source.

Alternatively (in the case of an electrical source), the speed could be maintained constant, and instead the voltage supplied to the radiation source would be varied in correlation with the topology of the stenosis.

The program according to which the apparatus is operated can be based on a feed-back principle, as indicated above, i.e. data relating to the size and general topology of the lesion at hand will be recorded by contrast X-ray (or other means such ultra sound, etc.), and fed into the control unit, wherein a suitable sequence of movements and radiation energies of the radiation source is calculated.

Figure 8:
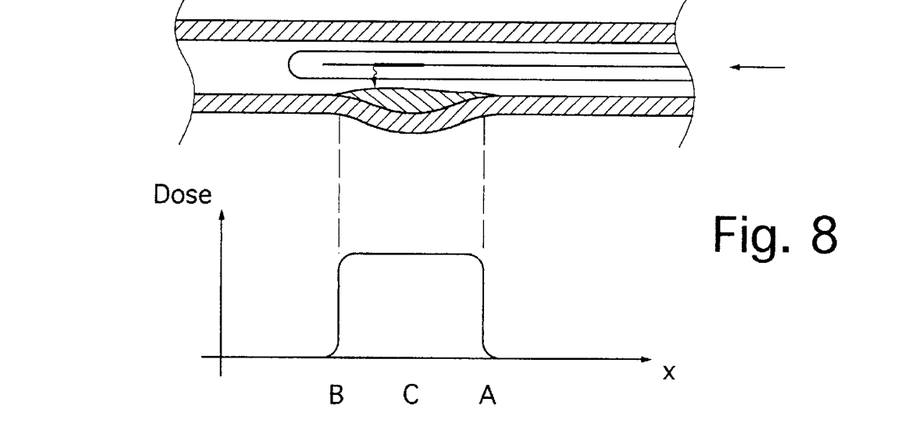
FIG. 8 shows a stenosis after PTCA and a dose profile for treating said stenosis usning an on-off method at constant dose.

In FIG. 8 a stenosis is shown below which a graph is drawn showing how a controlled dose is achieved by moving the radiation source inside the vessel past the stenosis, switching the radiation source on at A, and switching off at point B. This will bring about a control in terms of the longitudinal extension, but obviously the stenosis will receive more radiation per unit volume in the thinner regions at A and B respectively, than at the thicker mid-point C.

Therefore, it is desirable to control the dose at each point. This can be achieved in at least two ways, as will be described with reference to FIGS. 9 and 10.

Figure 9:
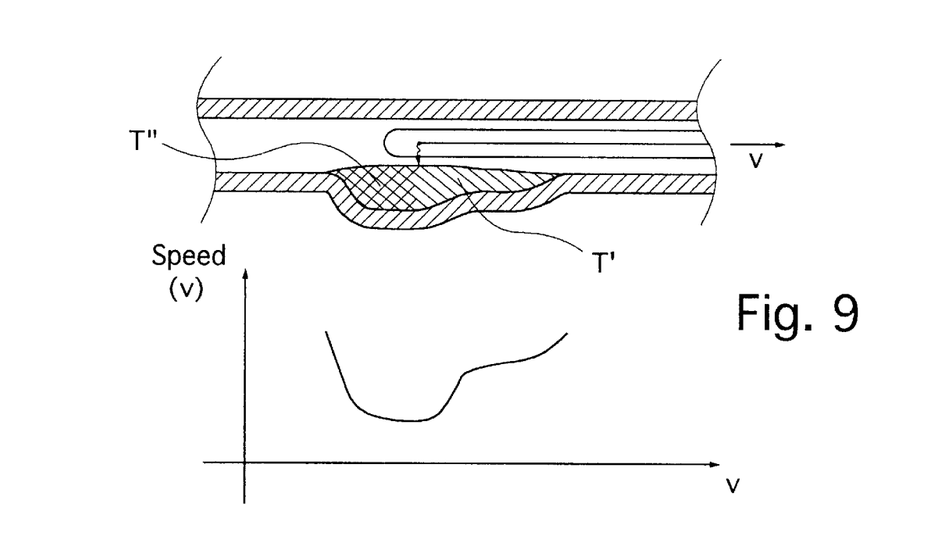
FIG. 9 shows a dose profile achieved by controlling the speed of movement of the radiation source.

In FIG. 9 a stenosis is shown having a thinner part T' and a thicker part T". By controlling the speed of the movement past the stenosis according to the velocity profile shown under the picture of the stenosis, an essentially uniform dose, i.e. amount of radiation per unit volume, is achieved. The speed profile is calculated by the control unit using the input data from the X-ray or ultrasound or other investigation obtained previously.

Figure 10:
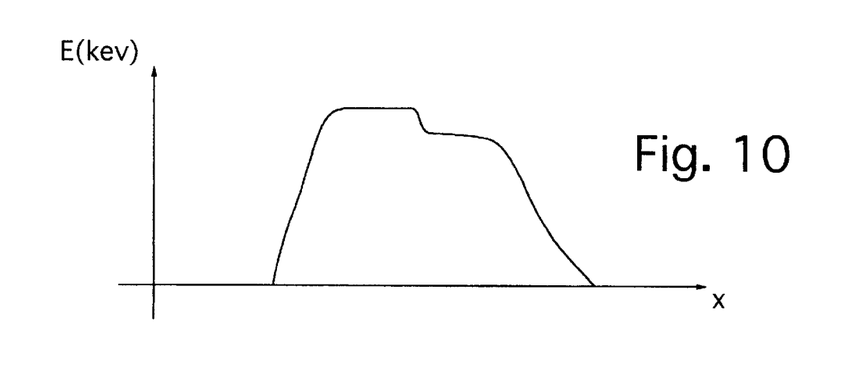
FIG. 10 shows a dose profile achieved by controlling the radiation energy from the radiation source.

In FIG. 10 an alternative method is shown. The same stenosis can be treated by controlling the radiation energy at a constant speed of the radiation source. Thus, the diagram shows an energy profile for the emitted radiation vs location of the radiation source at the stenosis. As can be seen the intensity is higher over the region T" where the stenosis is thicker.

The energy is varied by changing the energizing voltage, which is taken care of by the control unit in accordance with the calculated profile.

Figure 16:
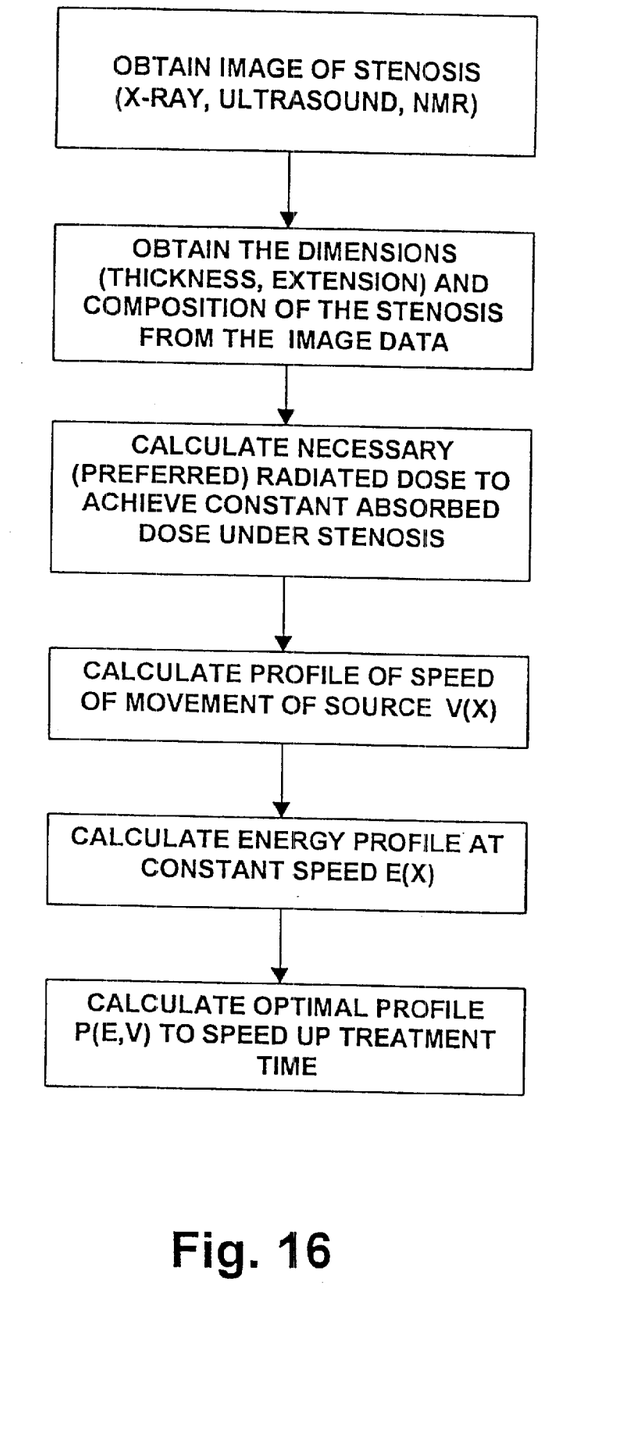
FIG. 16 is a simple flow chart for arriving at an optimal dose profile.

In FIG. 16 a flow chart is shown that schematically illustrates the control program in the control unit. Thus, first the stenosis must be characterized in terms of its size (and optionally its composition). Such data are obtained by X-ray (yields an image of the stenosis, primarily its longitudinal extension and thickness), ultra sound investigation (yields cross section area at various points along its length, and composition), or NMR (composition data).

Once the data concerning the stenosis (dimensions and composition) has been acquired, a radiation dose at each selected point in the stenosis can be calculated. For this calculation there are commercial software programs available, and even freeware, such as PHOTCOEF, obtainable from AIC Software Inc. This program calculates the $x_o$ value for the stenosis, which obviously can vary at different points in the stenosis, depending on the composition.

Based on the calculated $x_o$ values, the radiation dose required to achieve the necessary and preferred radiated dose is calculated. Thereby, as already indicated previously, the dose can be controlled by controlling the speed of movement v(x) of the radiation source along the lesion. That is the speed v can be a function of position x. Alternatively, the dose can be controlled by varying the energy E as a function of position e along the lesion, E(x).

Since there is a maximum in the attainable energy output, it may be required to optimize the radiation profile P by combining the two approaches in order to achieve a sufficiently rapid treatment, i.e. P(v,x).

The invention will be exemplified by the following non-limiting example:

EXAMPLE

Figure 11:
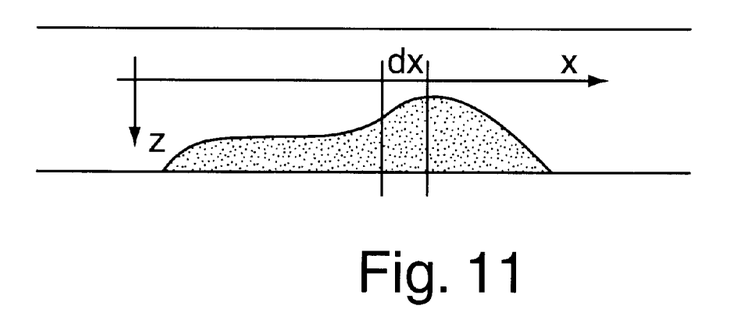
FIG. 11 illustrates the segmentation of an X-ray image for calculation purposes.

We use an X-ray picture of a coronary vessel with a stenosis as an example, see FIG. 11, which is a schematic representation of a so called angiogram.

From this FIG. one can easily obtain the thickness of the stenosis as a function of longitudinal displacement x. The material composition from e.g. IVUS (Intra Vascular Ultra Sound) may also be used as information to yield more accurate information for mass absorption data.

The mass absorption data may in practice be obtained by splitting the vessel and stenosis into segments of practical length, dx, as indicated in the figure. Thus, information of mass absorption coefficient as a function of distance z from the radiation source is known (which is assumed to be located in the center of the vessel) for each segment dx of the vessel.

Figure 12:
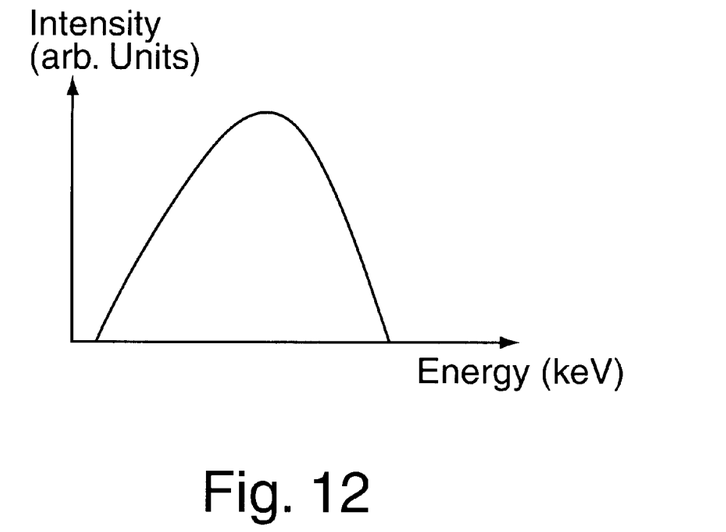
FIG. 12 shows a Bremsstrahlung profile for a radiation source.

Then, the energy distribution from the radiation source is considered known, either by calibrating or by design. An example of the distribution of the energy (the intensity of the radiation as a function of energy) is shown in FIG. 12. In this example only Brehmsstrahlung is shown for simplicity of explanation. Characteristic peaks of the radiation are easily taken care of as well.

The energy distribution is normalized (by integrating the intensity over energy) and the spectrum is split into segments dE (or fitted to a function or tabulated).

Figure 13:
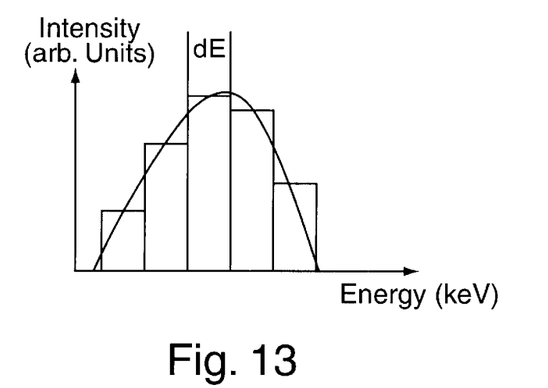
FIG. 13 shows segmentation of the energy profile for calculation purposes.

The order of this operation is arbitrary. The number of segments is arbitrary, and the energy segments dE must not be equal but can be optimized to yield an approximation with as high accurate as necessary. The method of doing so can be selected from a variety of known methods; the method shown in FIG. 13 is one of the crudest.

Now:

For each part of the energy spectrum, the relative intensity is know known.

For each segment dx of the vessel, material composition as a function of z is known.

Therefore mass absorption coefficient data as a function of z is for each energy part of the spectrum may easily be obtained; calculated by commercially available programs or obtained from tables (in the latter case an interpolation may be necessary)

For each segment dx we may then use the well established relationship $$I=I(O)\exp(z/z_o)$$

Where $z_o$ is the mass absorption coefficient which is dependent of material composition and energy of the radiation, I(O) is the intensity of the radiation at z=O and I is the intensity of the radiation as a function of distance z The absorbed intensity is then the intensity that is not transmitted. (The energy absorbed is the intensity loss per unit time)

Figure 14:
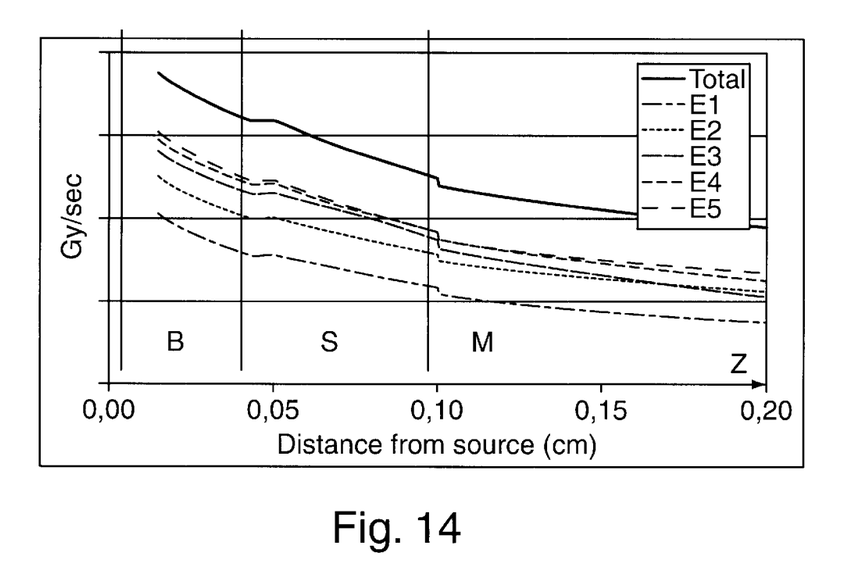
FIG. 14 shows calculated absorbed doses for different energies in the energy spectrum of FIG. 13.

As shown in FIG. 14, the location of the stenosis has been divided into three segments of different material characteristics, blood B, stenosis S and muscle tissue M, each having their own mass absorption coefficients.

However, in practice (for calculation accuracy reasons) also each material is divided the z-direction into a number of small segments, and the transmitted energy/intensity through these segments are calculated, and thereby one obtains how much energy is absorbed in the segment.

Each segment dz has its own material and energy specific mass absorption coefficient.

Finally this calculation is made for all energies dE according to the division of the energy spectrum shown in FIG. 13.

As an example, the deposited energy for different parts of the energy is shown in FIG. 14.

The energy deposited into blood B, stenosis S and muscle tissue M for five different energy segments dE (E1–E5) as a function of distance. Mass absorption values for the stenosis have been estimated only in this example. The centre of the radiation source is assumed to be positioned 0.5 mm from the vessel wall with blood flowing between the source and the stenosis. It is obvious that this model may be further refined with for example a portion of vessel wall material inserted between the stenosis and the muscle tissue. The energy scale is logarithmic in the above example Finally, as the irradiated length of the vessel from a point source can be estimated or measured, (and the same is not critical as long as this length is small compared to the length of the part of the vessel to be treated) it is easy to calculate the speed at each segment dx of the vessel, i.e. each point x.

EXAMPLE

The dose to be delivered at a position of say z=2 mm is considered to be 20 Gy A 0.1 mm long portion of the vessel is irradiated when the source is not moving. The dose rate is 2 Gy/second per 0.1 mm vessel length from the above calculation.

The time to deliver 20 Gy to 0.1 mm vessel length is then 10 seconds, i.e. the speed of movement will be 0.1/10 mm/sec=0.01 mm/sec. A typical stenosis of uniform thickness and a length of 3 mm would then require 300 seconds to treat i.e. 5 minutes.

Figure 15:
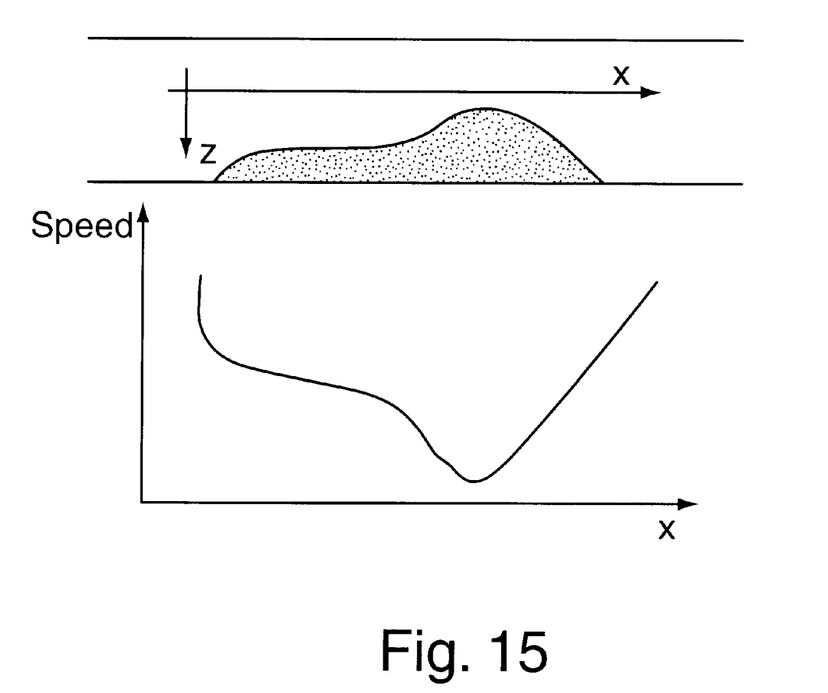
FIG. 15 shows a dose profile achieved by varying the speed of movement of the radiation source.

The above calculations are, as said above, done for each segment of the stenosis and a corresponding velocity profile could be as shown in FIG. 15, which is an example of the calculated velocity profile (velocity as a function of x), after extracting information and converting it into movement in order to achieve a constant dose at a specific depth. Other optimum energy depositions may be found be future research and may likewise be calculated and achieved by this method.

The above example has not used the possibility to modulate the energy of an electrically activated radiation source. It is easily conceived that by varying the energy similar calculations may be performed. Thereby, it is possible to further optimize the treatment with respect to treatment time, wanted and unwanted energy deposition and so forth.

What is claimed is:

1. An apparatus for the controlled delivery of ionizing radiation to a therapy location, comprising:
    an elongated member suitable for insertion into the body of a patient;
    a source of ionizing radiation provided near a distal end of said elongated member;
    a driving unit to move the elongated member;
    a control unit for controlling the operation of said driving unit; and
    a shielded housing into which the source of ionizing radiation can be withdrawn,
    wherein an X-ray detector is provided for calibration purposes and function checks.

2. The apparatus as claimed in claim 1, wherein the elongated member is selected from a wire (6), a needle.

3. The apparatus as claimed in claim 1, wherein the source of ionizing radiation is a radioactive isotope.

4. The apparatus as claimed in claim 1, wherein the source of ionizing radiation is an electrically energized radiation source.

5. The apparatus as claimed in claim 1, wherein the control unit is programmable to cause the driving unit to move the source of ionizing radiation at controlled and variable speeds at the therapy location in the longitudinal direction, forwards as well as backwards.

6. The apparatus as claimed in claim 1, wherein the control unit is programmable to cause the driving unit to rotate the radiation source.

7. The apparatus as claimed in claim 1, further comprising: a catheter having a lumen in which said elongated member is insertable.

8. The apparatus as claimed in claim 1, wherein the driving unit comprises a pair of guide rolls bearing against the elongated member for causing the movement thereof.

9. The apparatus as claimed in claim 1, wherein the driving unit comprises a clamp in which a proximal end of the elongated member is insertable, and which is coupled so as to enable a rotation of the elongated member.

10. The apparatus as claimed in claim 1, further comprising a shielding member provided to prevent radiation from the source of ionizing radiation from penetration into healthy tissue.

11. The apparatus as claimed in claim 1, wherein the control unit includes a memory for storing information relating to properties of the body to be treated.

12. A method of providing a controlled dose of ionizing radiation to a lesion at a therapy location, comprising:
    providing an elongated member suitable for insertion into the body of a patient;
    withdrawing a source of ionizing radiation from a shielded housing;
    calibrating said source of ionizing radiation with a radiation detector;
    attaching said source of ionizing radiation near a distal end of said elongated member;
    coupling said elongated member to a driving unit capable of causing a controlled movement of the elongated member at said lesion;
    coupling said driving unit to a programmable control unit for controlling the operation of said driving unit;
    providing said control unit with information relating to the properties of the lesion to be treated;
    generating a running sequence for the driving unit based upon said information;
    inserting said elongated member in said body and locating the source of ionizing radiation at said lesion to be treated with radiation; and
    running said driving unit under control of the control unit, in accordance with the programmed information relating to the lesion.

13. The method as claimed in claim 12, further comprising: obtaining the properties of the lesion to be treated by X-ray imaging, ultrasound imaging, NMR, or a combination of methods selected from the group consisting of X-ray imaging, ultrasound imaging, and NMR.

14. The method as claimed in claim 12, wherein the lesion is a stenosis in a coronary vessel.

* * * * *